United States Patent [19]

Skerra et al.

[11] Patent Number: 5,849,576
[45] Date of Patent: Dec. 15, 1998

[54] TETRACYCLINE PROMOTER FOR THE STRINGENTLY REGULATED PRODUCTION OF RECOMBINANT PROTEINS IN PROKARYOTIC CELLS

[75] Inventors: Arne Skerra, Cheruskerweg; Christina Wardenberg, Frankfurt am Main, both of Germany

[73] Assignee: Max-Planck-Gesellschaft Zur Forderung Der Wissenschaften E.V.

[21] Appl. No.: 737,316

[22] PCT Filed: May 17, 1995

[86] PCT No.: PCT/EP95/01862

§ 371 Date: Nov. 12, 1996

§ 102(e) Date: Nov. 12, 1996

[87] PCT Pub. No.: WO95/32295

PCT Pub. Date: Nov. 30, 1995

[30] Foreign Application Priority Data

May 19, 1994 [DE] Germany ........................ 44 17 598.1

[51] Int. Cl.[6] ............................ C12N 15/63; C12N 15/64; C12N 15/70
[52] U.S. Cl. ................. 435/320.1; 435/69.7; 435/252.3; 536/23.4; 536/24.1
[58] Field of Search ............................. 435/69.7, 252.3, 435/252.33, 254.11, 320.1, 325, 849; 536/23.4, 23.7, 24.1

[56] References Cited

U.S. PATENT DOCUMENTS 5,464,758   11/1995   Gossen et al. ......................... 435/69.1

FOREIGN PATENT DOCUMENTS 39 34 454 A1   4/1991   Germany.

94/04672   3/1994   WIPO.

OTHER PUBLICATIONS

Bertrand et al. Construction of a single–copy promoter vector and its use in analysis of regulation of the transposon Tn10 tetracycline resistance determinant. Journal of Bacteriology. vol. 158, No. 3, pp. 910–919, Jun. 1984.

Gatz et al. Regulation of a modified CaMV 35S promoter by the Tn10–encoded Tet repressor in transgenic tobacco. Molecular and General Genetics. vol. 227, pp. 229–237, 1991.

Chopra et al. Sensitive biological detection method for tetracyclines using a tetA–lac7 fusion system. Antimicrobial Agents and Chemotheraphy. vol. 34, No. 1, pp. 111–116, Jan. 1990.

Wray et al., Journal of Bacteriology, "Identification of Repressor Binding Sites Controlling . . . ", vol. 156, Dec. 1993, No. 3.

Schiweck et al, Proteins, "Fermenter Production of an Artificial Fab Fragement, Rationally . . . ", 23:561–565 (1995).

Skerra, Gene, "Use of the tetracycline promoter for the tightly regulated production of a murine . . . ", 151 (1994) 131–135.

*Primary Examiner*—Stephen Walsh
*Assistant Examiner*—Daryl A. Basham
*Attorney, Agent, or Firm*—Nikaido Marmelstein Murray & Oram LLP

[57] ABSTRACT

The present invention concerns a prokaryotic vector which contains a regulatable expression control sequence that can be repressed by the repressor of the tetracycline resistance gene, a prokaryotic cell transformed with this vector and the use of the vector or the cell in a process for the production of polypeptides in prokaryotes by genetic engineering.

25 Claims, 17 Drawing Sheets

Fig. 1a/1

```
              P
              f         B
              l         a
              M         l
              I         I
       ACCCGACACCATCGAATGGCCAGATGATTAATTCCTAATTTTTGTTGACACTCTATCATT
    1  ----------+---------+---------+---------+---------+---------+60
       TGGGCTGTGGTAGCTTACCGGTCTACTAATTAAGGATTAAAAACAACTGTGAGATAGTAA
``` a:   ThrArgHisHisArgMetAlaArgEndLeuIleProAsnPheCysEndHisSerIleIle   -
b:     ProAspThrIleGluTrpProAspAspEndPheLeuIlePheValAspThrLeuSerLeu -
c:       ProThrProSerAsnGlyGlnMetIleAsnSerEndPheLeuLeuThrLeuTyrHisEnd -

```
       GATAGAGTTATTTTACCACTCCCTATCAGTGATAGAGAAAAGTGAAATGAATAGTTCGAC
   61  ----------+---------+---------+---------+---------+---------+120
       CTATCTCAATAAAATGGTGAGGGATAGTCACTATCTCTTTTCACTTTACTTATCAAGCTG
``` a:   AspArgValIleLeuProLeuProIleSerAspArgGluLysEndAsnGluEndPheAsp   -
b:     IleGluLeuPheTyrHisSerLeuSerValIleGluLysSerGluMetAsnSerSerThr -
c:       EndSerTyrPheThrThrProTyrGlnEndEndArgLysValLysEndIleValArgGln -

```
              X
              b
              a
              I
       AAAAATCTAGATAACGAGGGCAAAAAATGAAAAAGACAGCTATCGCGATTGCAGTGGCAC
  121  ----------+---------+---------+---------+---------+---------+180
       TTTTTAGATCTATTGCTCCCGTTTTTTACTTTTTCTGTCGATAGCGCTAACGTCACCGTG
``` a:   LysAsnLeuAspAsnGluGlyLysLysEndLysArgGlnLeuSerArgLeuGlnTrpHis   -
b:     LysIleEndIleThrArgAlaLysAsnGluLysAspSerTyrArgAspCysSerGlyThr -
c:       LysSerArgEndArgGlyGlnLysMetLysLysThrAlaIleAlaIleAlaValAlaLeu -

```
                                     E                       B
                             B S     c              S    K S a
                             s t     o              s    p m m
                             a u     R              t    n a H
                             I I     I              I    I I I
       TGGCTGGTTTCGCTACCGTAGCGCAGGCCTGAGACCAGAATTCGAGCTCGGTACCCGGGG
  181  ----------+---------+---------+---------+---------+---------+240
       ACCGACCAAAGCGATGGCATCGCGTCCGGACTCTGGTCTTAAGCTCGAGCCATGGGCCCC
```

Fig.1a/2

```
a:    TrpLeuValSerLeuProEndArgArgProGluThrArgIleArgAlaArgTyrProGly      -
b:       GlyTrpPheArgTyrArgSerAlaGlyLeuArgProGluPheGluLeuGlyThrArgGly   -
c:          AlaGlyPheAlaThrValAlaGlnAlaEndAspGlnAsnSerSerSerValProGlyAsp -
```

```
                        S     E
                        s     c                                   H
                        e     o                                   i
                        8  B  4                                   n
          X     SA      P3 s  7                                   d
          h     ac      s8 p  I                                   I
          o     lc      t7 M  I                                   I
          I     II      II I  I                                   I
                         /
          ATCCCTCGAGGTCGACCTGCAGGCAGCGCTTGGCGTCACCCGCAGTTCGGTGGTTAATAA
     241  ----------+---------+---------+---------+---------+---------+300
          TAGGGAGCTCCAGCTGGACGTCCGTCGCGAACCGCAGTGGGCGTCAAGCCACCAATTATT
```

```
a:       IleProArgGlyArgProAlaGlySerAlaTrpArgHisProGlnPheGlyGlyEndEnd   -
b:          SerLeuGluValAspLeuGlnAlaAlaLeuGlyValThrArgSerSerValValAsnLys -
c:             ProSerArgSerThrCysArgGlnArgLeuAlaSerProAlaValArgTrpLeuIleSer -

GCTTGACCTGTGAAGTGAAAAATGGCGCACATTGTGCGACATTTTTTTGTCTGCCGTTT
     301  ----------+---------+---------+---------+---------+---------+360
          CGAACTGGACACTTCACTTTTTACCGCGTGTAACACGCTGTAAAAAAACAGACGGCAAA
```

```
a:       AlaEndProValLysEndLysMetAlaHisIleValArgHisPhePheCysLeuProPhe   -
b:          LeuAspLeuEndSerGluLysTrpArgThrLeuCysAspIlePhePheValCysArgLeu -
c:             LeuThrCysGluValLysAsnGlyAlaHisCysAlaThrPhePheLeuSerAlaValTyr -

ACCGCTACTGCGTCACGGATCTCCACGCGCCCTGTAGCGGCGCATTAAGCGCGGCGGGTG
     361  ----------+---------+---------+---------+---------+---------+420
          TGGCGATGACGCAGTGCCTAGAGGTGCGCGGGACATCGCCGCGTAATTCGCGCCGCCCAC
```

```
a:       ThrAlaThrAlaSerArgIleSerThrArgProValAlaAlaHisEndAlaArgArgVal   -
b:          ProLeuLeuArgHisGlySerProArgAlaLeuEndArgArgIleLysArgGlyGlyCys -
c:             ArgTyrCysValThrAspLeuHisAlaProCysSerGlyAlaLeuSerAlaAlaGlyVal -

TGGTGGTTACGCGCAGCGTGACCGCTACACTTGCCAGCGCCCTAGCGCCCGCTCCTTTCG
     421  ----------+---------+---------+---------+---------+---------+480
          ACCACCAATGCGCGTCGCACTGGCGATGTGAACGGTCGCGGGATCGCGGGCGAGGAAAGC
```

```
a:       TrpTrpLeuArgAlaAlaEndProLeuHisLeuProAlaProEndArgProLeuLeuSer   -
b:          GlyGlyTyrAlaGlnArgAspArgTyrThrCysGlnArgProSerAlaArgSerPheArg -
```

Fig.1a/3

```
c:         ValValThrArgSerValThrAlaThrLeuAlaSerAlaLeuAlaProAlaProPheAla -
                                       N
                                       a
                                       e
                                       I
           CTTTCTTCCCTTCCTTTCTCGCCACGTTCGCCGGCTTTCCCCGTCAAGCTCTAAATCGGG
       481 ----------+---------+---------+---------+---------+---------+540
           GAAAGAAGGGAAGGAAAGAGCGGTGCAAGCGGCCGAAAGGGGCAGTTCGAGATTTAGCCC a:     LeuSerSerLeuProPheSerProArgSerProAlaPheProValLysLeuEndIleGly   -
    b:       PheLeuProPheLeuSerArgHisValArgArgLeuSerProSerSerSerLysSerGly -
    c:       PhePheProSerPheLeuAlaThrPheAlaGlyPheProArgGlnAlaLeuAsnArgGLy -

GGCTCCCTTTAGGGTTCCGATTTAGTGCTTTACGGCACCTCGACCCCAAAAAACTTGATT
       541 ----------+---------+---------+---------+---------+---------+600
           CCGAGGGAAATCCCAAGGCTAAATCACGAAATGCCGTGGAGCTGGGGTTTTTTGAACTAA a:     GlySerLeuEndGlySerAspLeuValLeuTyrGlyThrSerThrProLysAsnLeuIle   -
    b:       AlaProPheArgValProIleEndCysPheThrAlaProArgProGlnLysThrEndLeu -
    c:       LeuProLeuGlyPheArgPheSerAlaLeuArgHisLeuAspProLysLysLeuAspEnd -

AGGGTGATGGTTCACGTAGTGGGCCATCGCCCTGATAGACGGTTTTTCGCCCTTTGACGT
       601 ----------+---------+---------+---------+---------+---------+660
           TCCCACTACCAAGTGCATCACCCGGTAGCGGGACTATCTGCCAAAAAGCGGGAAACTGCA a:     ArgValMetValHisValValGlyHisArgProAspArgArgPhePheAlaLeuEndArg  -
    b:       GlyEndTrpPheThrEndTrpAlaIleAlaLeuIleAspGlyPheSerProPheAspVal -
    c:       GlyAspGlySerArgSerGlyProSerProEndEndThrValPheArgProLeuThrLeu -

TGGAGTCCACGTTCTTTAATAGTGGACTCTTGTTCCAAACTGGAACAACACTCAACCCTA
       661 ----------+---------+---------+---------+---------+---------+720
           ACCTCAGGTGCAAGAAATTATCACCTGAGAACAAGGTTTGACCTTGTTGTGAGTTGGGAT a:     TrpSerProArgSerLeuIleValAspSerCysSerLysLeuGluGlnHisSerThrLeu  -
    b:       GlyValHisValLeuEndEndTrpThrLeuValProAsnTrpAsnAsnThrGlnProTyr -
    c:       GluSerThrPhePheAsnSerGlyLeuLeuPheGlnThrGlyThrThrLeuAsnProIle -

TCTCGGTCTATTCTTTTGATTTATAAGGGATTTTGCCGATTTCGGCCTATTGGTTAAAAA
       721 ----------+---------+---------+---------+---------+---------+780
           AGAGCCAGATAAGAAAACTAAATATTCCCTAAAACGGCTAAAGCCGGATAACCAATTTTT a:     SerArgSerIleLeuLeuIleTyrLysGlyPheCysArgPheArgProIleGlyEndLys  -
    b:       LeuGlyLeuPhePheEndPheIleArgAspPheAlaAspPheGlyLeuLeuValLysLys -
```

Fig. 1a /4

```
c:              SerValTyrSerPheAspLeuEndGlyIleLeuProIleSerAlaTyrTrpLeuLysAsn  -

ATGAGCTGATTTAACAAAAATTTAACGCGAATTTTAACAAAATATTAACGTTTACAATTT
       781  ----------+----------+---------+---------+---------+---------+840
              TACTCGACTAAATTGTTTTTAAATTGCGCTTAAAATTGTTTTATAATTGCAAATGTTAAA a:            MetSerEndPheAsnLysAsnLeuThrArgIleLeuThrLysTyrEndArgLeuGlnPhe  -
b:              EndAlaAspLeuThrLysIleEndArgGluPheEndGlnAsnIleAsnValTyrAsnPhe -
c:                GluLeuIleEndGlnLysPheAsnAlaAsnPheAsnLysIleLeuThrPheThrIleSer  -

CAGGTGGCACTTTTCGGGGAAATGTGCGCGGAACCCCTATTTGTTTATTTTTCTAAATAC
       841  ----------+----------+---------+---------+---------+---------+900
              GTCCACCGTGAAAAGCCCCTTTACACGCGCCTTGGGGATAAACAAATAAAAAGATTTATG a:            GlnValAlaLeuPheGlyGluMetCysAlaGluProLeuPheValTyrPheSerLysTyr  -
b:              ArgTrpHisPheSerGlyLysCysAlaArgAsnProTyrLeuPheIlePheLeuAsnThr  -
c:                GlyGlyThrPheArgGlyAsnValArgGlyThrProIleCysLeuPhePheEndIleHis -

E
                                                                            a
                                                                            r
                                                                            I
              ATTCAAATATGTATCCGCTCATGAGACAATAACCCTGATAAATGCTTCAATAATATTGAA
       901  ----------+----------+---------+---------+---------+---------+960
              TAAGTTTATACATAGGCGAGTACTCTGTTATTGGGACTATTTACGAAGTTATTATAACTT a:            IleGlnIleCysIleArgSerEndAspAsnAsnProAspLysCysPheAsnAsnIleGlu -
b:              PheLysTyrValSerAlaHisGluThrIleThrLeuIleAsnAlaSerIleIleLeuLys -
c:                SerAsnMetTyrProLeuMetArgGlnEndProEndEndMetLeuGlnEndTyrEndLys -

AAAGGAAGAGTATGAGTATTCAACATTTCCGTGTCGCCCTTATTCCCTTTTTTGCGGCAT
       961  ----------+----------+---------+---------+---------+---------+1020
              TTTCCTTCTCATACTCATAAGTTGTAAAGGCACAGCGGGAATAAGGGAAAAAACGCCGTA a:            LysGlyArgValEndValPheAsnIleSerValSerProLeuPheProPheLeuArgHis -
b:              LysGluGluTyrGluTyrSerThrPheProCysArgProTyrSerLeuPheCysGlyIle -
c:                ArgLysSerMetSerIleGlnHisPheArgValAlaLeuIleProPhePheAlaAlaPhe -

TTTGCCTTCCTGTTTTTGCTCACCCAGAAACGCTGGTGAAAGTAAAAGATGCTGAAGATC
      1021  ----------+----------+---------+---------+---------+---------+1080
              AAACGGAAGGACAAAAACGAGTGGGTCTTTGCGACCACTTTCATTTTCTACGACTTCTAG a:            PheAlaPheLeuPheLeuLeuThrGlnLysArgTrpEndLysEndLysMetLeuLysIle -
b:              LeuProSerCysPheCysSerProArgAsnAlaGlyGluSerLysArgCysEndArgSer -
```

Fig.1a/5 c: CysLeuProValPheAlaHisProGluThrLeuValLysValLysAspAlaGluAspGln -

```
          AGTTGGGTGCACGAGTGGGTTACATCGAACTGGATCTCAACAGCGGTAAGATCCTTGAGA
     1081 ----------+----------+---------+---------+---------+---------+1140
          TCAACCCACGTGCTCACCCAATGTAGCTTGACCTAGAGTTGTCGCCATTCTAGGAACTCT
``` a: SerTrpValHisGluTrpValThrSerAsnTrpIleSerThrAlaValArgSerLeuArg -
b: ValGlyCysThrSerGlyLeuHisArgThrGlySerGlnGlnArgEndAspProEndGlu -
c: LeuGlyAlaArgValGlyTyrIleGluLeuAspLeuAsnSerGlyLysIleLeuGluSer -

```
                             X
                             m
                             n
                             I
          GTTTTCGCCCCGAAGAACGTTTTCCAATGATGAGCACTTTTAAAGTTCTGCTATGTGGCG
     1141 ----------+----------+---------+---------+---------+---------+1200
          CAAAAGCGGGGCTTCTTGCAAAAGGTTACTACTCGTGAAAATTTCAAGACGATACACCGC
``` a: ValPheAlaProLysAsnValPheGlnEndEndAlaLeuLeuLysPheCysTyrValAla -
b: PheSerProArgArgThrPheSerAsnAspGluHisPheEndSerSerAlaMetTrpArg -
c: PheArgProGluGluArgPheProMetMetSerThrPheLysValLeuLeuCysGlyAla -

```
                                                  B
                                                  c
                                                  g
                                                  I
          CGGTATTATCCCGTATTGACGCCGGGCAAGAGCAACTCGGTCGCCGCATACACTATTCTC
     1201 ----------+----------+---------+---------+---------+---------+1260
          GCCATAATAGGGCATAACTGCGGCCCGTTCTCGTTGAGCCAGCGGCGTATGTGATAAGAG
``` a: ArgTyrTyrProValLeuThrProGlyLysSerAsnSerValAlaAlaTyrThrIleLeu -
b: GlyIleIleProTyrEndArgArgAlaArgAlaThrArgSerProHisThrLeuPheSer -
c: ValLeuSerArgIleAspAlaGlyGlnGluGlnLeuGlyArgArgIleHisTyrSerGln -

```
                       S
                       c
                       a
                       I
          AGAATGACTTGGTTGAGTACTCACCAGTCACAGAAAAGCATCTTACGGATGGCATGACAG
     1261 ----------+----------+---------+---------+---------+---------+1320
          TCTTACTGAACCAACTCATGAGTGGTCAGTGTCTTTTCGTAGAATGCCTACCGTACTGTC
``` a: ArgMetThrTrpLeuSerThrHisGlnSerGlnLysSerIleLeuArgMetAlaEndGln -
b: GluEndLeuGlyEndValLeuThrSerHisArgLysAlaSerTyrGlyTrpHisAspSer -

Fig. 1a /6

```
c:       AsnAspLeuValGluTyrSerProValThrGluLysHisLeuThrAspGlyMetThrVal    -

G
                                            d
                                            i
                                            I
                                            I
         TAAGAGAATTATGCAGTGCTGCCATAACCATGAGTGATAACACTGCGGCCAACTTACTTC
   1321 ---------+---------+---------+---------+---------+---------+1380
         ATTCTCTTAATACGTCACGACGGTATTGGTACTCACTATTGTGACGCCGGTTGAATGAAG a:       EndGluAsnTyrAlaValLeuProEndProEndValIleThrLeuArgProThrTyrPhe    -
b:         LysArgIleMetGlnCysCysHisAsnHisGluEndEndHisCysGlyGlnLeuThrSer  -
c:           ArgGluLeuCysSerAlaAlaIleThrMetSerAspAsnThrAlaAlaAsnLeuLeuLeu -

P
                    v
                    u
                    I
         TGACAACGATCGGAGGACCGAAGGAGCTAACCGCTTTTTTGCACAACATGGGGGATCATG
   1381 ---------+---------+---------+---------+---------+---------+1440
         ACTGTTGCTAGCCTCCTGGCTTCCTCGATTGGCGAAAAAACGTGTTGTACCCCCTAGTAC a:       EndGlnArgSerGluAspArgArgSerEndProLeuPheCysThrThrTrpGlyIleMet    -
b:         AspAsnAspArgArgThrGluGlyAlaAsnArgPhePheAlaGlnHisGlyGlySerCys  -
c:           ThrThrIleGlyGlyProLysGluLeuThrAlaPheLeuHisAsnMetGlyAspHisVal -

TAACTCGCCTTGATCGTTGGGAACCGGAGCTGAATGAAGCCATACCAAACGACGAGCGTG
   1441 ---------+---------+---------+---------+---------+---------+1500
         ATTGAGCGGAACTAGCAACCCTTGGCCTCGACTTACTTCGGTATGGTTTGCTGCTCGCAC a:       EndLeuAlaLeuIleValGlyAsnArgSerEndMetLysProTyrGlnThrThrSerVal    -
b:         AsnSerProEndSerLeuGlyThrGlyAlaGluEndSerHisThrLysArgArgAlaEnd  -
c:           ThrArgLeuAspArgTrpGluProGluLeuAsnGluAlaIleProAsnAspGluArgAsp -

F
                                  s
                                  p
                                  I -
         ACACCACGATGCCTGTAGCAATGGCAACAACGTTGCGCAAACTATTAACTGGCGAACTAC
   1501 ---------+---------+---------+---------+---------+---------+1560
         TGTGGTGCTACGGACATCGTTACCGTTGTTGCAACGCGTTTGATAATTGACCGCTTGATG a:       ThrProArgCysLeuEndGlnTrpGlnGlnArgCysAlaAsnTyrEndLeuAlaAsnTyr    -
```

Fig. 1a /7 b:            HisHisAspAlaCysSerAsnGlyAsnAsnValAlaGlnThrIleAsnTrpArgThrThr    -
c:            ThrThrMetProValAlaMetAlaThrThrLeuArgLysLeuLeuThrGlyGluLeuLeu    -

```
                             M
                             u
                             n
                             I
      TTACTCTAGCTTCCCGGCAACAATTgATAGACTGGATGGAGGCGGATAAAGTTGCAGGAC
 1561 ---------+---------+---------+---------+---------+---------+1620
      AATGAGATCGAAGGGCCGTTGTTAAcTATCTGACCTACCTCCGCCTATTTCAACGTCCTG
``` a:        LeuLeuEndLeuProGlyAsnAsnEndEndThrGlyTrpArgArgIleLysLeuGlnAsp    -
b:         TyrSerSerPheProAlaThrIleAspArgLeuAspGlyGlyGlyEndSerCysArgThr   -
c:          ThrLeuAlaSerArgGlnGlnLeuIleAspTrpMetGluAlaAspLysValAlaGlyPro  -

```
                        B
                        g
                        l
                        I
      CACTTCTGCGCTCGGCCCTTCCGGCTGGCTGGTTTATTGCTGATAAATCTGGAGCCGGTG
 1621 ---------+---------+---------+---------+---------+---------+1680
      GTGAAGACGCGAGCCGGGAAGGCCGACCGACCAAATAACGACTATTTAGACCTCGGCCAC
``` a:        HisPheCysAlaArgProPheArgLeuAlaGlyLeuLeuLeuIleAsnLeuGluProVal   -
b:         ThrSerAlaLeuGlyProSerGlyTrpLeuValTyrCysEndEndIleTrpSerArgEnd  -
c:          LeuLeuArgSerAlaLeuProAlaGlyTrpPheIleAlaAspLysSerGlyAlaGlyGlu -

```
                                                                P
                                                                f
                                                                l
                                                                l
                                                                1
                  G                                             1
                  s                                             0
                  u                                             8
                  I                                             I
      AGCGTGGCTCTCGCGGTATCATTGCAGCACTGGGGCCAGATGGTAAGCCCTCCCGTATCG
 1681 ---------+---------+---------+---------+---------+---------+1740
      TCGCACCGAGAGCGCCATAGTAACGTCGTGACCCCGGTCTACCATTCGGGAGGGCATAGC
``` a:        SerValAlaLeuAlaValSerLeuGlnHisTrpGlyGlnMetValSerProProValSer   -
b:         AlaTrpLeuSerArgTyrHisCysSerThrGlyAlaArgTrpEndAlaLeuProTyrArg  -
c:          ArgGlySerArgGlyIleIleAlaAlaLeuGlyProAspGlyLysProSerArgIleVal -

Fig.1a/8

```
                                   E
                                   a
                                   m
                                   1
                                   1
                                   0
                                   5
                                   I
        TAGTTATCTACACGACGGGGAGTCAGGCAACTATGGATGAACGAAATAGACAGATCGCTG
   1741 ----------+----------+---------+---------+---------+---------+1800
        ATCAATAGATGTGCTGCCCCTCAGTCCGTTGATACCTACTTGCTTTATCTGTCTAGCGAC a:      EndLeuSerThrArgArgGlyValArgGlnLeuTrpMetAsnGluIleAspArgSerLeu     -
b:         SerTyrLeuHisAspGlyGluSerGlyAsnTyrGlyEndThrLysEndThrAspArgEnd  -
c:            ValIleTyrThrThrGlySerGlnAlaThrMetAspGluArgAsnArgGlnIleAlaGlu -

AGATAGGTGCCTCACTGATTAAGCATTGGTAGGAATTAATGATGTCTCGTTTAGATAAAA
   1801 ----------+----------+---------+---------+---------+---------+1860
        TCTATCCACGGAGTGACTAATTCGTAACCATCCTTAATTACTACAGAGCAAATCTATTTT a:      ArgEndValProHisEndLeuSerIleGlyArgAsnEndEndCysLeuValEndIleLys    -
b:         AspArgCysLeuThrAspEndAlaLeuValGlyIleAsnAspValSerPheArgEndLys -
c:            IleGlyAlaSerLeuIleLysHisTrpEndGluLeuMetMetSerArgLeuAspLysSer -

GTAAAGTGATTAACAGCGCATTAGAGCTGCTTAATGAGGTCGGAATCGAAGGTTTAACAA
   1861 ----------+----------+---------+---------+---------+---------+1920
        CATTTCACTAATTGTCGCGTAATCTCGACGAATTACTCCAGCCTTAGCTTCCAAATTGTT a:      ValLysEndLeuThrAlaHisEndSerCysLeuMetArgSerGluSerLysValEndGln   -
b:         EndSerAspEndGlnArgIleArgAlaAlaEndEndGlyArgAsnArgArgPheAsnAsn -
c:            LysValIleAsnSerAlaLeuGluLeuLeuAsnGluValGlyIleGluGlyLeuThrThr -

N
                                                       s
                                                       p
                                                       I
        CCCGTAAACTCGCCCAGAAGCTAGGTGTAGAGCAGCCTACATTGTATTGGCATGTAAAAA
   1921 ----------+----------+---------+---------+---------+---------+1980
        GGGCATTTGAGCGGGTCTTCGATCCACATCTCGTCGGATGTAACATAACCGTACATTTTT a:      ProValAsnSerProArgSerEndValEndSerSerLeuHisCysIleGlyMetEndLys    -
b:         ProEndThrArgProGluAlaArgCysArgAlaAlaTyrIleValLeuAlaCysLysLys -
c:            ArgLysLeuAlaGlnLysLeuGlyValGluGlnProThrLeuTyrTrpHisValLysAsn -
```

Fig. 1a/9

```
                           B
                           p
                           u
                           l
                           o
                           I
        ATAAGCGGGCTTTGCTCGACGCCTTAGCCATTGAGATGTTAGATAGGCACCATACTCACT
   1981 ---------+---------+---------+---------+---------+---------+2040
        TATTCGCCCGAAACGAGCTGCGGAATCGGTAACTCTACAATCTATCCGTGGTATGAGTGA
``` a:     IleSerGlyLeuCysSerThrProEndProLeuArgCysEndIleGlyThrIleLeuThr -
b:       EndAlaGlyPheAlaArgArgLeuSerHisEndAspValArgEndAlaProTyrSerLeu -
c:         LysArgAlaLeuLeuAspAlaLeuAlaIleGluMetLeuAspArgHisHisThrHisPhe -

```
                     E                        S
                     c                        n
                     o                        a
                     N                        B
                     I                        I
        TTTGCCCTTTAGAAGGGGAAAGCTGGCAAGATTTTTTACGTAATAACGCTAAAAGTTTTA
   2041 ---------+---------+---------+---------+---------+---------+2100
        AAACGGGAAATCTTCCCCTTTCGACCGTTCTAAAAAATGCATTATTGCGATTTTCAAAAT
``` a:     PheAlaLeuEndLysGlyLysAlaGlyLysIlePheTyrValIleThrLeuLysValLeu -
b:       LeuProPheArgArgGlyLysLeuAlaArgPhePheThrEndEndArgEndLysPheEnd -
c:         CysProLeuGluGlyGluSerTrpGlnAspPheLeuArgAsnAsnAlaLysSerPheArg -

```
        GATGTGCTTTACTAAGTCATCGCGATGGAGCAAAAGTACATTTAGGTACACGGCCTACAG
   2101 ---------+---------+---------+---------+---------+---------+2160
        CTACACGAAATGATTCAGTAGCGCTACCTCGTTTTCATGTAAATCCATGTGCCGGATGTC
``` a:     AspValLeuTyrEndValIleAlaMetGluGlnLysTyrIleEndValHisGlyLeuGln -
b:       MetCysPheThrLysSerSerArgTrpSerLysSerThrPheArgTyrThrAlaTyrArg -
c:         CysAlaLeuLeuSerHisArgAspGlyAlaLysValHisLeuGlyThrArgProThrGlu -

```
        AAAAACAGTATGAAACTCTCGAAAATCAATTAGCCTTTTTATGCCAACAAGGTTTTTCAC
   2161 ---------+---------+---------+---------+---------+---------+2220
        TTTTTGTCATACTTTGAGAGCTTTTAGTTAATCGGAAAAATACGGTTGTTCCAAAAAGTG
``` a:     LysAsnSerMetLysLeuSerLysIleAsnEndProPheTyrAlaAsnLysValPheHis -
b:       LysThrValEndAsnSerArgLysSerIleSerLeuPheMetProThrArgPhePheThr -
c:         LysGlnTyrGluThrLeuGluAsnGlnLeuAlaPheLeuCysGlnGlnGlyPheSerLeu -

```
                           BN                   Fig.1a/10
                           ss
                           mi
                           II
                           /
         TAGAGAATGCATTATATGCACTCAGCGCaGTGGGGCATTTTACTTTAGGTTGCGTATTGG
    2221 ---------+---------+---------+---------+---------+---------+2280
         ATCTCTTACGTAATATACGTGAGTCGCGtCACCCCGTAAAATGAAATCCAACGCATAACC a:      EndArgMetHisTyrMetHisSerAlaGlnTrpGlyIleLeuLeuEndValAlaTyrTrp   -
    b:        ArgGluCysIleIleCysThrGlnArgSerGlyAlaPheTyrPheArgLeuArgIleGly -
    c:          GluAsnAlaLeuTyrAlaLeuSerAlaValGlyHisPheThrLeuGlyCysValLeuGlu -

AAGATCAAGAGCATCAAGTCGCTAAAGAAGAAAGGGAAACACCTACTACTGATAGTATGC
    2281 ---------+---------+---------+---------+---------+---------+2340
         TTCTAGTTCTCGTAGTTCAGCGATTTCTTCTTTCCCTTTGTGGATGATGACTATCATACG a:      LysIleLysSerIleLysSerLeuLysLysLysGlyLysHisLeuLeuLeuIleValCys    -
    b:        ArgSerArgAlaSerSerArgEndArgArgLysGlyAsnThrTyrTyrEndEndTyrAla  -
    c:          AspGlnGluHisGlnValAlaLysGluGluArgGluThrProThrThrAspSerMetPro -

S
                                                   t
                                                   y
                                                   I
         CGCCATTATTACGACAAGCTATCGAATTATTTGATCACCAAGGTGCAGAGCCAGCCTTCT
    2341 ---------+---------+---------+---------+---------+---------+2400
         GCGGTAATAATGCTGTTCGATAGCTTAATAAACTAGTGGTTCCACGTCTCGGTCGGAAGA a:      ArgHisTyrTyrAspLysLeuSerAsnTyrLeuIleThrLysValGlnSerGlnProSer    -
    b:        AlaIleIleThrThrSerTyrArgIleIleEndSerProArgCysArgAlaSerLeuLeu  -
    c:          ProLeuLeuArgGlnAlaIleGluLeuPheAspHisGlnGlyAlaGluProAlaPheLeu -

B                N
               s                d
               g                e
               I                I
         TATTCGGCCTTGAATTGATCATATGCGGATTAGAAAAACAACTTAAATGTGAAAGTGGGT
    2401 ---------+---------+---------+---------+---------+---------+2460
         ATAAGCCGGAACTTAACTAGTATACGCCTAATCTTTTGTTGAATTTACACTTTCACCCA a:      TyrSerAlaLeuAsnEndSerTyrAlaAspEndLysAsnAsnLeuAsnValLysValGly   -
    b:        IleArgProEndIleAspHisMetArgIleArgLysThrThrEndMetEndLysTrpVal -
    c:          PheGlyLeuGluLeuIleIleCysGlyLeuGluLysGlnLeuLysCysGluSerGlySer -
```

Fig.1a/11

```
                                                    S
                                                    p
                                                    e
                                                    I
            CTTAAAAGCAGCATAACCTTTTTCCGTGATGGTAACTTCACTAGTTTAAAAGGATCTAGG
      2461 ----------+---------+---------+---------+---------+---------+2520
            GAATTTTCGTCGTATTGGAAAAAGGCACTACCATTGAAGTGATCAAATTTTCCTAGATCC
``` a:         LeuLysSerSerIleThrPhePheArgAspGlyAsnPheThrSerLeuLysGlySerArg    -
b:           LeuLysAlaAlaEndProPheSerValMetValThrSerLeuValEndLysAspLeuGly  -
c:             EndLysGlnHisAsnLeuPheProEndTrpEndLeuHisEndPheLysArgIleEndVal -

```
            TGAAGATCCTTTTTGATAATCTCATGACCAAAATCCCTTAACGTGAGTTTTCGTTCCACT
      2521 ----------+---------+---------+---------+---------+---------+2580
            ACTTCTAGGAAAAACTATTAGAGTACTGGTTTTAGGGAATTGCACTCAAAAGCAAGGTGA
``` a:         EndArgSerPheLeuIleIleSerEndProLysSerLeuAsnValSerPheArgSerThr   -
b:           GluAspProPheEndEndSerHisAspGlnAsnProLeuThrEndValPheValProLeu -
c:             LysIleLeuPheAspAsnLeuMetThrLysIleProEndArgGluPheSerPheHisEnd -

```
            GAGCGTCAGACCCCGTAGAAAAGATCAAAGGATCTTCTTGAGATCCTTTTTTTCTGCGCG
      2581 ----------+---------+---------+---------+---------+---------+2640
            CTCGCAGTCTGGGGCATCTTTTCTAGTTTCCTAGAAGAACTCTAGGAAAAAAAGACGCGC
``` a:         GluArgGlnThrProEndLysArgSerLysAspLeuLeuGluIleLeuPhePheCysAla   -
b:           SerValArgProArgArgLysAspGlnArgIlePheLeuArgSerPhePheSerAlaArg -
c:             AlaSerAspProValGluLysIleLysGlySerSerEndAspProPhePheLeuArgVal -

```
                                                H
                                                g
                                                i
                                                E
                                                I
                                                I
            TAATCTGCTGCTTGCAAACAAAAAAACCACCGCTACCAGCGGTGGTTTGTTTGCCGGATC
      2641 ----------+---------+---------+---------+---------+---------+2700
            ATTAGACGACGAACGTTTGTTTTTTTGGTGGCGATGGTCGCCACCAAACAAACGGCCTAG
``` a:         EndSerAlaAlaCysLysGlnLysAsnHisArgTyrGlnArgTrpPheValCysArgIle   -
b:           AsnLeuLeuLeuAlaAsnLysLysThrThrAlaThrSerGlyGlyLeuPheAlaGlySer -
c:             IleCycCysLeuGlnThrLysLysProProLeuProAlaValValCysLeuProAspGln -

Fig. 1a/12

```
          AAGAGCTACCAACTCTTTTTCCGAAGGTAACTGGCTTCAGCAGAGCGCAGATACCAAATA
     2701 ----------+----------+----------+----------+----------+----------+2760
          TTCTCGATGGTTGAGAAAAAGGCTTCCATTGACCGAAGTCGTCTCGCGTCTATGGTTTAT
``` a: LysSerTyrGlnLeuPhePheArgArgEndLeuAlaSerAlaGluArgArgTyrGlnIle  -
b:   ArgAlaThrAsnSerPheSerGluGlyAsnTrpLeuGlnGlnSerAlaAspThrLysTyr -
c:     GluLeuProThrLeuPheProLysValThrGlyPheSerArgAlaGlnIleProAsnThr -

```
          CTGTCCTTCTAGTGTAGCCGTAGTTAGGCCACCACTTCAAGAACTCTGTAGCACCGCCTA
     2761 ----------+----------+----------+----------+----------+----------+2820
          GACAGGAAGATCACATCGGCATCAATCCGGTGGTGAAGTTCTTGAGACATCGTGGCGGAT
``` a: LeuSerPheEndCysSerArgSerEndAlaThrThrSerArgThrLeuEndHisArgLeu  -
b:   CysProSerSerValAlaValValArgProProLeuGlnGluLeuCysSerThrAlaTyr -
c:     ValLeuLeuValEndProEndLeuGlyHisHisPheLysAsnSerValAlaProProThr -

```
                                  A
                                  l
                                  W
                                  N
                                  I
          CATACCTCGCTCTGCTAATCCTGTTACCAGTGGCTGCTGCCAGTGGCGATAAGTCGTGTC
     2821 ----------+----------+----------+----------+----------+----------+2880
          GTATGGAGCGAGACGATTAGGACAATGGTCACCGACGACGGTCACCGCTATTCAGCACAG
``` a: HisThrSerLeuCysEndSerCysTyrGlnTrpLeuLeuProValAlaIleSerArgVal  -
b:   IleProArgSerAlaAsnProValThrSerGlyCysCysGlnTrpArgEndValValSer -
c:     TyrLeuAlaLeuLeuIleLeuLeuProValAlaAlaAlaSerGlyAspLysSerCysLeu -

```
          TTACCGGGTTGGACTCAAGACGATAGTTACCGGATAAGGCGCAGCGGTCGGGCTGAACGG
     2881 ----------+----------+----------+----------+----------+----------+2940
          AATGGCCCAACCTGAGTTCTGCTATCAATGGCCTATTCCGCGTCGCCAGCCCGACTTGCC
``` a: LeuProGlyTrpThrGlnAspAspSerTyrArgIleArgArgSerGlyArgAlaGluArg  -
b:   TyrArgValGlyLeuLysThrIleValThrGlyEndGlyAlaAlaValGlyLeuAsnGly -
c:     ThrGlyLeuAspSerArgArgEndLeuProAspLysAlaGlnArgSerGlyEndThrGly -

```
          GGGGTTCGTGCACACAGCCCAGCTTGGAGCGAACGACCTACACCGAACTGAGATACCTAC
     2941 ----------+----------+----------+----------+----------+----------+3000
          CCCCAAGCACGTGTGTCGGGTCGAACCTCGCTTGCTGGATGTGGCTTGACTCTATGGATG
``` a: GlyValArgAlaHisSerProAlaTrpSerGluArgProThrProAsnEndAspThrTyr  -
b:   GlyPheValHisThrAlaGlnLeuGlyAlaAsnAspLeuHisArgThrGluIleProThr -
c:     GlySerCysThrGlnProSerLeuGluArgThrThrTyrThrGluLeuArgTyrLeuGln -

Fig. 1a/13

```
        AGCGTGAGCTATGAGAAAGCGCCACGCTTCCCGAAGGGAGAAAGGCGGACAGGTATCCGG
   3001 ----------+---------+---------+---------+---------+---------+3060
        TCGCACTCGATACTCTTTCGCGGTGCGAAGGGCTTCCCTCTTTCCGCCTGTCCATAGGCC
``` a:     SerValSerTyrGluLysAlaProArgPheProLysGlyGluArgArgThrGlyIleArg   -
b:       AlaEndAlaMetArgLysArgHisAlaSerArgArgGluLysGlyGlyGlnValSerGly  -
c:         ArgGluLeuEndGluSerAlaThrLeuProGluGlyArgLysAlaAspArgTyrProVal -

```
        TAAGCGGCAGGGTCGGAACAGGAGAGCGCACGAGGGAGCTTCCAGGGGGAAACGCCTGGT
   3061 ----------+---------+---------+---------+---------+---------+3120
        ATTCGCCGTCCCAGCCTTGTCCTCTCGCGTGCTCCCTCGAAGGTCCCCCTTTGCGGACCA
``` a:     EndAlaAlaGlySerGluGlnGluSerAlaArgGlySerPheGlnGlyGluThrProGly  -
b:       LysArgGlnGlyArgAsnArgArgAlaHisGluGlyAlaSerArgGlyLysArgLeuVal -
c:         SerGlyArgValGlyThrGlyGluArgThrArgGluLeuProGlyGlyAsnAlaTrpTyr -

```
        ATCTTTATAGTCCTGTCGGGTTTCGCCACCTCTGACTTGAGCGTCGATTTTTGTGATGCT
   3121 ----------+---------+---------+---------+---------+---------+3180
        TAGAAATATCAGGACAGCCCAAAGCGGTGGAGACTGAACTCGCAGCTAAAAACACTACGA
``` a:     IlePheIleValLeuSerGlyPheAlaThrSerAspLeuSerValAspPheCysAspAla  -
b:       SerLeuEndSerCysArgValSerProProLeuThrEndAlaSerIlePheValMetLeu -
c:         LeuTyrSerProValGlyPheArgHisLeuEndLeuGluArgArgPheLeuEndCysSer -

```
        CGTCAGGGGGGCGGAGCCTATGGAAAAACGCCAGCAACGCGGCCTTTTTACGGTTCCTGG
   3181 ----------+---------+---------+---------+---------+---------+3240
        GCAGTCCCCCCGCCTCGGATACCTTTTTGCGGTCGTTGCGCCGGAAAAATGCCAAGGACC
``` a:     ArgGlnGlyGlyGlyAlaTyrGlyLysThrProAlaThrArgProPheTyrGlySerTrp  -
b:       ValArgGlyAlaGluProMetGluLysArgGlnGlnArgGlyLeuPheThrValProGly -
c:         SerGlyGlyArgSerLeuTrpLysAsnAlaSerAsnAlaAlaPheLeuArgPheLeuAla -

```
        CCTTTTGCTGGCCTTTTGCTCACATG
   3241 ----------+---------+------ 3266
        GGAAAACGACCGGAAAACGAGTGTAC
``` a:     ProPheAlaGlyLeuLeuLeuThr      -
b:       LeuLeuLeuAlaPheCysSerHis    -
c:         PheCysTrpProPheAlaHisMet  -

Fig. 2 a.
```
                                        <<<<<<<<  >>>>>>>>              << <
CCATCGAATGGCCAGATGATTAATTCCTAATTTTTGTTGACACTCTATCATTGATAGAGTTATTTTACCACTCCC  75
                                    -35                    -10         +1
```

```
<<<<< >>>>>> >>                         XbaI
TATCAGTGATAGAGAAAAGTGAAATGAATAGTTCGACAAAAATCTAGATAACGAGGGCAAAAAATGAAAAAGACA 150
       *** TetA: MetAsnSerSerThrLysIleEnd     **** OmpA: MetLysLysThr
```

```
                                          StuI BsaI  EcoRI  SstI KpnI
GCTATCGCGATTGCAGTGGCACTGGCTGGTTTCGCTACCGTAGCGCAGGCCTGAGACCAGAATTCGAGCTCGGTA 225
AlaIleAlaIleAlaValAlaLeuAlaGlyPheAlaThrValAlaGlnAlaEnd
```

```
SmaI BamHI XhoI  SalI  PstI  Eco47III                          HindIII
CCCGGGGATCCCTCGAGGTCGACCTGCAGGCAGCGCTTGGCGTCACCCGCAGTTCGGTGGTTAATAAGCTTGACC 300
         Strep tag: SerAlaTrpArgHisProGlnPheGlyGlyEnd
```

```
        <<<<<<<<  <<<<<    >>>>> >>>>>>>
TGTGAAGTGAAAAATGGCGCACATTGTGCGACATTTTTTTTGTCTGCCGTTTACCGCTACTGCGTCACGGATCTC 375
                               mRNA End
``` b.
```
                       ****
AGATAGGTGCCTCACTGATTAAGCATTGGTAGGAATTAATGATCTCTCGTTTAGATAAAAGTAAAGTGATTAACA
    Bla: ...SerLeuIleLysHisTrpEnd   TetR: MetSerArgLeuAspLysSerLys...
```

TETRACYCLINE PROMOTER FOR THE STRINGENTLY REGULATED PRODUCTION OF RECOMBINANT PROTEINS IN PROKARYOTIC CELLS

SUMMARY OF THE INVENTION

The present application is the national stage entry of PCT/EP95/01862 filed on May 17, 1995.

The present invention concerns a prokaryotic vector which contains a regulatable expression control sequence which can be repressed by the repressor of the tetracycline resistance gene, a prokaryotic cell transformed with this vector and the use of the vector or the cell in a process for the production of polypeptides in prokaryotes by genetic engineering.

Inducible promoter systems have proven to be very suitable for the production of heterologous proteins in *E. coli* since synthesis of the recombinant gene product often has a toxic effect on the bacterial cell which impairs its growth and viability. In particular when the foreign protein is secreted into the periplasmatic space of the host cell, it is advisable to ensure a strict repression of the promoter not only in the course of the procedures for producing the vector but also in order to achieve high cell densities with the transformed bacteria before the actual protein production. The bacterial secretion of antibody fragments is a typical example in this respect since, due to the heterologous gene expression, a toxic and lytic effect is observed on the bacterial cell (Plükthun and Skerra, Methods Enzymol. 178 (1989), 497–515).

An inducible promoter system that is used particularly frequently is the lac promoter and its derivatives that can be induced by isopropyl-β-D-thiogalactopyranoside (IPTG) e.g. the mutant lacUV5 or the tac fusion promoter (Reznikoff and Gold (1986), in: Maximizing gene expression, Butterworth Publishers, Stoneham, Mass.). The use of the lac promoter to produce antibody fragments in bacteria by genetic engineering is described for example by Skerra (dissertation, LMU Munich, Faculty for Chemistry and Pharmacy, 1983).

However, the strength of the transcription by the lac promoter is coupled to the genotype and metabolism of the host cell via the endogenous concentration of lac repressor molecules on the one hand and via the catabolite repression effect on the other hand. Thus when using a lac expression system considerable variations in the expression level are observed with a given vector depending on the host strain used. This may be either due to a reduced inducibility—particularly if the lac repressor is coded chromosomally as well as by a plasmid and thus is present in excessive amounts—or to a dying of the cells or a loss of plasmid before the induction as a result of inadequate repression.

In addition to the lac promoter other regulatable promoter systems have also been used, but, most of them have considerable disadvantages especially if a moderate secretion of the foreign gene product or an expression at a reduced temperature is desired in order to favour the protein folding process. Therefore there is a great need for the provision of a prokaryotic expression control sequence which is largely decoupled from the individual properties of the bacterial host cell and can be reversibly induced in a simple and cost-effective manner.

Plasmid vectors are described in a publication by De la Torre et al. (Plasmid 12 (1984), 103–110) in which the gene expression is partially regulated by tetracycline. These vectors contain the regulatory region of the tetracycline resistance gene from the transposon Tn10. This region originally causes the expression of the tetracycline resistance gene in one direction and the expression of the tetracycline repressor structural gene in the other (Bertrand et al., Gene 23 (1983), 149–156). In an interaction with the operator the tetracycline repressor protein inhibits the expression in both directions and is thus subject to autoregulation. The repression of a foreign gene instead of the tetracycline resistance gene under the control of this tetracycline promoter is achieved by co-transformation with a compatible plasmid which contains the tetracycline repressor gene which is likewise under the control of the tetracycline promoter. In host cells containing the two plasmids an up to 8-4-fold repression of the expression of a foreign gene was found in the absence of tetracycline. Such a low repression is completely inadequate for the production by genetic engineering of proteins with a toxic effect on the bacterial cell so that this system has to date had no practical application at all.

An object of the present invention is to provide an expression vector system for the production of recombinant proteins in prokaryotic organisms in which the disadvantages of the state of the art are at least partially eliminated.

This object is achieved by the provision of a prokaryotic vector comprising (a) a regulatable expression control sequence which can be repressed by a tetracycline repressor protein and (b) a tetracycline repressor structural gene in operative linkage with an expression control sequence which cannot be repressed by a tetracycline repressor protein.

DESCRIPTION OF THE PREFERRED EMBODIMENTS

The vector according to the invention differs from the tetracycline expression system known from the state of the art in that the tetracycline repressor is put under the control of an independent promoter and thus can no longer control its own synthesis. As a result a drastically improved repression is surprisingly achieved during the expression of a foreign gene under the control of the regulatable expression control sequence. Preferably a tetracycline repressor structural gene, e.g. the tetracycline repressor gene from the transposon Tn10 (Bertrand et al., Gene 23 (1983), 149–156), is located on the vector according to the invention in an operative linkage with a constitutive expression control sequence i.e. with a non-regulatable expression control sequence, for example with the promoter of the β-lactamase gene responsible for resistance to ampicillin.

In the non-induced state the tetracycline expression system according to the invention exhibits a considerably better repression than the lac expression system. This is manifested in a considerably improved growth behaviour and in an increased viability of bacteria that are transformed with a gene which codes for a polypeptide that is toxic to the host organism such as e.g. an antibody fragment. A further advantage of the expression system according to the invention is that the expression of a heterologous polypeptide is almost identical in the diverse *E. coli* host strains. Moreover, no significant influence of the nutrient medium on the expression of the heterologous polypeptide was observed. These advantages of the expression system according to the invention are already clearly recognizable in experiments on a laboratory scale, however, they occur to a considerable greater extent in experiments on a fermenter scale. The expression system according to the invention can therefore be used successfully for the recombinant production of polypeptides under industrial conditions.

The vector according to the invention is a prokaryotic vector i.e. a vector that is capable of propagation in a prokaryotic host cell. Examples of such vectors are plasmid vectors, bacteriophage lambda vectors, cosmid vectors and single-stranded filamentous bacteriophage vectors (cf. Sambrook et al., Molecular Cloning. A Laboratory Manual, 2nd Ed., Cold Spring Harbor Laboratory Press (1989), chapters 1–4 and 17). The vector according to the invention is preferably a circular plasmid, in particular a multicopy plasmid of which more than 10 copies are present in the host cell. The plasmid vector has an origin of replication that is suitable for the respective prokaryotic host cell e.g. a ColE1 or p15A origin of replication for *E. coli*. In addition the vector according to the invention preferably contains an antibiotic resistance gene e.g. an ampicillin, kanamycin or chloroamphenicol resistance gene in order to enable the selection of host cells that contain the vector.

The vector according to the invention contains a regulatable expression control sequence which can be repressed by the repressor of the tetracycline resistance gene. The tetracycline repressor is a protein which, in the absence of tetracycline or tetracycline derivatives, binds to the regulatory region of the tetracycline promoter region and represses the expression by this promoter. The repressor effect is abolished in the presence of tetracycline or tetracycline derivatives (Degenkolb et al., Antimicrob. Agents Chemother. 35 (1991), 1591–1595).

The expression control sequence of the vector according to the invention that can be repressed by a tetracycline repressor protein preferably contains the nucleotide sequence shown in SEQ ID NO.1 or a functional variant thereof. The nucleotide sequence shown in SEQ ID NO.1 corresponds to nucleotides 19 to 101 in FIG. 2a. The term "functional variant" means that the expression control sequence contains one, preferably two, functional tetracycline repressor binding sites which can for example be located between positions −35 and −10 or +1 to +19 of the expression control sequence (relative to the transcription start site) (cf. FIG. 2a).

The regulatable expression control sequence of the vector according to the invention particularly preferably contains the palindromic sections between nucleotides −31 to −13 or/and +1 to +19 (relative to the transcription start site) of the nucleotide sequence shown in SEQ ID NO. 1 and FIG. 2a with the base sequences 5'-ACTCTATCATTGATAGAGT-3' [SEQ ID NO.3] and 5'-TCCCTATCAGTGATAG-3' [SEQ ID NO.4] or DNA sequences with equivalent binding properties for the tetracycline repressor as functional tetracycline repressor binding sites.

The vector according to the invention in addition preferably contains a multiple cloning site in operative linkage with the expression control system that can be repressed by a tetracycline repressor protein. Foreign genes which are intended to be expressed by the expression system according to the invention can be cloned into this multiple cloning site which is also denoted polylinker and preferably contains several singular restriction cleavage sites for the respective vector.

The vector according to the invention can also contain a sequence coding for a signal peptide which is in operative linkage with the expression control sequence that can be repressed by a tetracycline repressor protein. Examples of suitable signal sequences are the OmpA and the PhoA signal sequences. Further suitable signal sequences are described for example by Winnacker in "Gene und Klone, Eine Einfuhrung in die Gentechnologie (1985), VCH Verlagsgesellschaft mbH, Weinheim", on pages 254 ff or by Watson "Compilation of published signal sequences", Nucl. Acids Res. 12 (1984), 5145–5164, respectively.

Secretion of the gene product coded by the foreign gene into the periplasm of the host cell with cleavage of the signal peptide is achieved by fusing the signal peptide coding sequence with a foreign gene inserted into the vector.

In addition the vector according to the invention preferably contains a transcription termination sequence in operative linkage with the expression control sequence that can be repressed by a tetracycline repressor protein in which case the transcription termination sequence, for example the lipoprotein transcription terminator, is located on the vector according to the invention in such a way that transcription of a gene that can be transcribed under the expression control of the tetracycline promoter ends at the terminator.

In order to facilitate the purification of a heterologous polypeptide which is produced by the tetracycline expression system, the vector according to the invention can additionally contain a nucleotide sequence coding for an affinity peptide in operative linkage with the expression control sequence that can be repressed by a tetracycline repressor protein. It is expedient that the sequence coding for the affinity peptide is located in the vector according to the invention in such a manner that it is fused with the C-terminus of a foreign gene inserted into the vector. Examples of suitable affinity peptides are an oligo-histidine peptide, in particular a sequence of 5 or 6 successive histidine residues which allows purification of bacterially expressed foreign proteins by metal chelate affinity chromatography (Hochuli et al., Bio/Technology (1988), 1321–1325) or a streptavidin binding peptide (Schmidt and Skerra, Protein Eng. 6 (1993), 109–122) which allows purification of the foreign protein by affinity chromatography with streptavidin agarose using very mild elution conditions. A particularly preferred streptavidin binding peptide also denoted "strep-tag" has the amino acid sequence Ser-Ala-Trp-Arg-His-Pro-Gln-Phe-Gly-Gly [SEQ ID NO. 5].

A further subject matter of the present invention is a vector which contains at least one foreign gene coding for a heterologous polypeptide in operative linkage with the expression control sequence that can be repressed by a tetracycline repressor protein. The foreign gene can be optionally present as a fusion with a sequence coding for a signal peptide or/and with a sequence coding for an affinity peptide. The term "heterologous" means that the foreign gene codes neither for the tetracycline resistance protein nor for the tetracycline repressor protein. The gene preferably codes for a polypeptide that is toxic to a prokaryotic cell and whose expression must be kept as low as possible in the non-induced state. Examples of such toxic products are antibody fragments. However, the expression system according to the invention can be used not only for the said examples but generally for the expression of any desired proteins, especially mammalian proteins.

The vector according to the invention can also contain several foreign genes under the control of a tetracycline promoter. An example of this is the expression vector pASK85-D1.3 (cf. FIG. 3) which contains the genes for the heavy and light chain of an antibody Fab fragment under the control of the tetracycline promoter.

A particularly preferred example of a vector according to the invention is the plasmid pASK75 which has the nucleotide sequence stated in FIG. 1a and SEQ ID NO.2 and is shown diagramatically in FIG. 1b. The genetic elements that this plasmid contains are a ColEI DNA origin of replication (ori), the β-lactamase gene (bla), the structural gene of the tetracycline repressor (tetR) under the control of the β-lactamase promoter, the intergenic region of the filamentous phage f1 (f1-IG), the promoter/operator region of the tetracycline resistance gene from the transposon Tn10 (tetP/O), a DNA sequence coding for the OmpA signal peptide, a polylinker, a DNA sequence coding for the streptavidin binding peptide (strep-tag) and the lipoprotein transcription terminator ($t_{lpp}$). These genetic elements are operatively linked to one another so that an expression vector can be provided by suitable insertion of a foreign gene into the polylinker which enables an efficient expression of foreign genes in prokaryotic host cells even if the polypeptides coded by the foreign gene represent a gene product that is toxic to the cell.

Furthermore the invention concerns a prokaryotic cell containing (a) a gene coding for a heterologous polypeptide in operative linkage with a regulatable expression control sequence which can be repressed by a tetracycline repressor protein and (b) a tetracycline repressor gene in operative linkage with an expression control sequence which cannot be repressed by a tetracycline repressor protein. This cell is preferably transformed with at least one copy of a vector according to the invention. The prokaryotic cell is preferably a gram-negative cell, particularly preferably an enterobacterial cell (e.g. salmonella, Escherichia) and most preferably an E. coli cell.

The vector according to the invention and the cell according to the invention can be used in a process for the production of polypeptides in prokaryotes by genetic engineering.

A further subject matter of the present invention is a process for the production of polypeptides in a prokaryotic cell by genetic engineering which is characterized in that (i) a cell is provided containing (a) at least one gene coding for a heterologous polypeptide in operative linkage with a regulatable expression control sequence that can be repressed by a tetracycline repressor protein and (b) a tetracycline repressor structural gene in operative linkage with an expression control sequence that cannot be repressed by a tetracycline repressor protein, (ii) the cell from (i) is cultured in a suitable medium under conditions which lead to an expression of the gene coding for the heterologous polypeptide and (iii) the heterologous polypeptide is isolated from the cell or from the medium.

The process according to the invention can be carried out in such a way that a host cell is used which contains the regulatable expression control sequence and the tetracycline repressor gene—as described above—on a single vector. On the other hand one can of course also use a host cell in which the regulatable expression control sequence and the tetracycline repressor gene are not on a single vector e.g. on two different vectors that are compatible with one another. Yet another possibility of carrying out the process according to the invention is to use a host cell which contains a vector with the foreign gene under the control of the tetracycline promoter and an episomal or chromosomal copy of the tetracycline repressor gene under the control of an independent promoter that cannot be repressed by the repressor.

The culture of the cell in step (ii) of the process according to the invention is preferably carried out in such a manner that the expression of the gene coding for the heterologous polypeptide is extensively repressed until a predetermined cell density has been reached i.e. in the absence of an inducer for the regulatable expression control sequence and that the expression of the foreign gene is not induced until the predetermined cell density has been reached. When the expression control sequence is fully induced it is possible to achieve a maximum expression of the gene products that are toxic to the cell. On the other hand it is possible to achieve an only partial induction of the expression control sequence which is desirable in some cases by adding small amounts of the inducer.

The regulatable expression control sequence is preferably induced by addition of tetracycline or a tetracycline derivative as inducer. The effect of adding the inducer is to abolish the repression of the regulatable expression control sequence by the tetracycline repressor protein.

Anhydrotetracycline is preferably used as the inducer. This compound is a commercially available substance which is effective at extremely low concentrations of for example 5 to 500 μg inducer per liter medium and furthermore only has a slight antibiotic effect (Olivia et al., Antimicrob. Agents Chemother. 36 (1992), 913–919). Therefore the use of tetracycline or tetracycline derivatives as an inducer is more economic than the use of IPTG in an expression system based on the lac promoter.

Concentrations of 100 to 250 μg/l anhydrotetracycline are preferred for a complete induction. Concentrations of 10 to 50 μg/l anhydrotetracycline are preferred for a partial induction.

A further advantage of the process according to the invention is that the production of polypeptides by genetic engineering using the tetracycline expression system can also be carried out with high efficiency in a minimal medium e.g. a glucose minimal medium (cf. Sambrook et al. (1989), supra, page A3). Minimal media are preferably used which contain 0.1 to 10% particularly preferably 1 to 7% and most preferably 2 to 5% of a C source on a weight basis in addition to mineral components (e.g. $Na^+$, $K^+$, $Ca^{2+}$, $Mg^{2+}$, $NH_4^+$, $Cl^-$, $SO_4^{2-}$, $PO_4^{3-}$).

The use of minimal media in the process according to the invention can on the one hand be carried out such that a nutrient medium with the total desired amount of the C source be added first in which the cells are then cultured. On the other hand part of the C source can also be added later during the fermentation in which case this addition is preferably regulated depending on the cell growth. A detailed description of the culture of transformed bacterial cells in minimal media is given by Riesenberg (Curr. Opin. Biotechnol. 2 (1991), 380–384). Reference is herewith made to the working techniques described in this literature reference.

The invention is further elucidated by the following examples, figures and sequence protocols.

BRIEF DESCRIPTION OF THE DRAWINGS

FIG. 1a shows the complete nucleotide sequence of plasmid pASK75 in a double-stranded form including the restriction sites [SEQ ID NO:2], FIG. 2a shows the nucleotide sequence of the total regulatory region on pASK75 [SEQ ID NO.6], FIG. 2b shows the artificially produced intercistronic region between the bla gene and the tetR structural gene on pASK75 [SEQ ID NO.7]

SEQ ID NO.1 shows the nucleotide sequence of the tetracycline promoter/operator region (corresponding to nucleotides 19 to 101 in FIG. 2a) and SEQ ID NO.2 shows the complete nucleotide sequence of the plasmid pASK75.

EXAMPLES

Example 1

Vector Construction

Figure 1B:
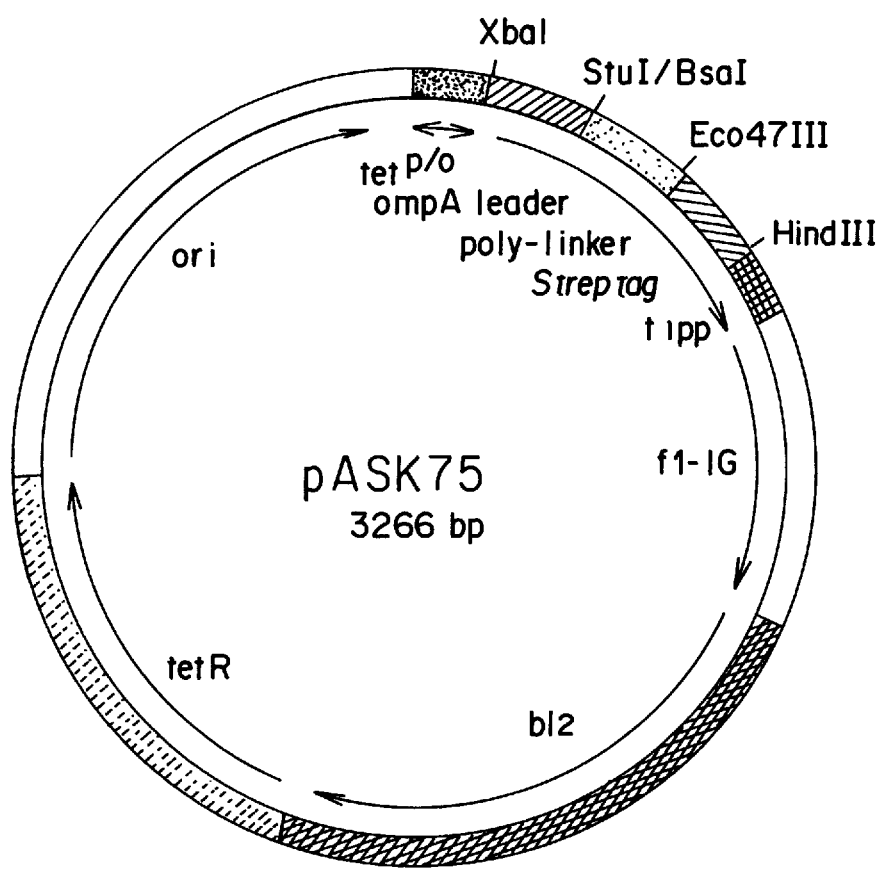
FIG. 1b shows a schematic representation of the vector pASK75.

The vector pASK75 shown in FIG. 1a and FIG. 1b which contains the tetracycline promoter/operator region and the tetracycline repressor gene was constructed from the lac promoter plasmid pASK60-strep (Schmidt and Skerra, Protein Eng. 6 (1993), 109–122). The expression cassette of pASK75 (the DNA sequence located between the XbaI and HindIII restriction sites, cf. FIG. 2a) is identical to that of pASK60-strep and is composed of a gene fragment that codes for the OmpA signal peptide with its translation initiation site, a polylinker and the strep-tag region coding for the streptavidin binding peptide.

pASK75 was constructed from pASK60-strep using standard methods (Sambrook et al. (1989), supra). Firstly the entire segment on pASK60-strep which contained the lacI gene and the lac promoter/operator was replaced by a short fragment from pWH1012 (Sizemore et al., Nucl. Acids Res. 18 (1990), 2875–2880) containing the tetracycline promoter region. The double methionine codon at the 5' end of the tetR reading frame was removed together with the XbaI restriction site that was originally directly adjacent. The tetR structural gene that was removed from the plasmid pWH520 (Berens et al., J. Biol. Chem. 267 (1992), 1945–1952) was inserted directly downstream of the modified translational stop codon for the β-lactamase gene. The XbaI restriction site at the beginning of the coding region was eliminated by mutagenesis. A singular SpeI restriction site was introduced downstream of the tetR reading frame and the Eco47III site in the tetR structural gene as well as an AseI site in the β-lactamase gene were removed.

The nucleotide sequence and the restriction sites in pASK75 are shown in FIG. 1a. The location of the genetic elements on pASK75 is shown schematically in FIG. 1b. tetP/O is the promoter/operator region, strep-tag is the nucleotide sequence coding for a streptavidin binding peptide, $t_{lpp}$ is the lipoprotein transcription terminator, bla is the β-lactamase gene, tetR is the structural gene of the tet repressor, ori is a ColE1 origin of replication, f1-IG is the intergenic reaction from the filamentous phage f1. In addition FIG. 1b shows the singular restriction sites for XbaI and HindIII which flank the expression cassette as well as the preferably suitable restriction sites for the insertion of foreign genes between the OmpA signal sequence and the strep-tag affinity peptide.

pASK75 contains a tandem ribosomal binding site for an efficient translation initiation. A structural gene can be fused with the OmpA signal sequence (e.g. via the StuI or BsaI restriction site) which enables the gene product to be secreted into the periplasm. On the other hand the structural gene can also be inserted into the XbaI site with simultaneous reconstruction of the second translation initiation site for expression into the cytoplasm.

FIG. 2a shows the nucleotide sequence of the complete regulatory region of pASK75 beginning with the tetA promoter in which the "−35" and "−10" consensus sequences as well as the starting site for transcription can be seen. The palindromic patterns in the promoter region corresponding to the two tetracycline repressor binding sites in the promoter region and the terminator structure are shown by open parantheses above the nucleotide sequence. The Shine Dalgarno elements are labelled with asterisks.

The tetracycline repressor gene is decoupled from the tetracycline promoter on pASK75. For this purpose the structural gene of the tetracycline repressor including its Shine Dalgarno sequence was inserted directly downstream of the constitutively expressed β-lactamase gene which leads to a transcriptional fusion.

FIG. 2b shows the artificial intercistronic region between the bla gene and the tetR structural gene on pASK75. The Shine Dalgarno sequence of the tetR gene is labelled with asterisks.

Example 2

Gene Expression

Figure 3:
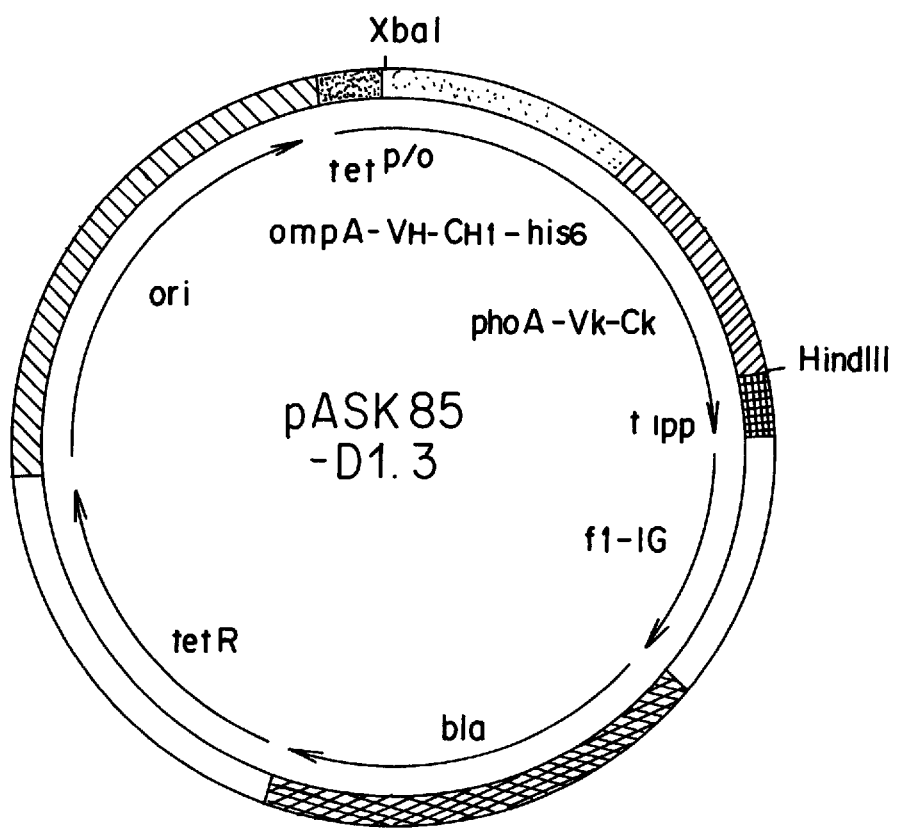
FIG. 3 shows a schematic representation of the vector pASK85-D1.3.

The properties of the tetracycline expression system were examined using the secretion of antibody fragments in *E. coli* as an example. The plasmid pASK85-D1.3 was used as an expression vector which contains the structural genes for the two polypeptide chains of an Fab antibody fragment with the variable domains of the anti-lysozyme antibody D1.3 (Boulot et al., J. Mol. Biol. 213 (1990), 617–619). The gene for the heavy chain as well as the gene for the light chain are under the common transcriptional control of the tetracycline promoter/operator and each are preceded by a bacterial signal peptide (OmpA, PhoA). The expression plasmid pASK85-D1.3 was constructed from the base vector pASK75 using the plasmid pASK84-D1.3 (Skerra, Gene 141 (1994), 79–84). FIG. 3 shows a schematic representation of the plasmid pASK85-D1.3. OmpA-$V_H$-$C_H$1-his 6 is a region which codes for a fusion polypeptide composed of an OmpA signal peptide, the fragment of the heavy antibody chain and a C-terminal $His_6$ sequence. PhoA-$V_K$-$C_K$ is a region which codes for a fusion polypeptide composed of a PhoA signal peptide and the fragment of the light antibody chain. The other genetic elements have the same meaning as stated in FIG. 1b.

Figure 4A:
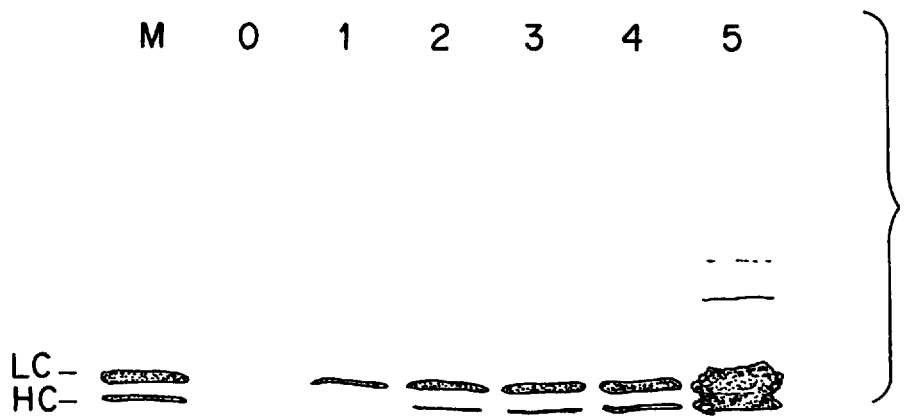
FIG. 4a shows the time course of induction of the synthesis of an antibody Fab fragment under the control of a tetracycline promoter and FIG. 4b shows the dependence of the synthesis of the antibody Fab fragment on the host strain.

The time course of an induction of antibody fragment synthesis by pASK85-D1.3 is shown in FIG. 4a in a Western blot of the total cell protein. The blots were stained using commercial antisera (rabbit anti-mouse Ig and porcine anti-rabbit Ig alkaline phosphatase conjugate, Dako, Hamburg, GER) and the dyes nitro blue tetrazolium (Sigma, Deisenhofen, GER) and 5-bromo-4-chloro-3-indolyl phosphate, toluidine salt (Boehringer Mannheim GmbH, GER) according to standard methods (Sambrook et al. (1989), supra). The cells were previously cultured at 22° C. up to the mid log phase and then the promoter was induced by addition of 200 μg anhydrotetracycline per liter medium. One hour afterwards it was possible to clearly detect both chains of the Fab fragment. Their amount increased continuously during the course of the induction period (4h) and even increased further during a further incubation overnight. Comparison with the purified recombinant Fab fragment showed that both Fab precursors were processed quantitatively. An estimation showed that about 20 mg/l Ig protein had been synthesized after 3 to 4 h induction.

Lane 0 of FIG. 4a shows a sample taken immediately before the induction. Lanes 1 to 4 show samples 1 to 4 h after induction, lane 5 shows a sample after an overnight incubation, lane M shows ca 1 μg purified recombinant Fab fragment. LC and HC denote the light and heavy chain of the Ig fragment.

A comparison of the expression of the Ig protein by the plasmid pASK85-D1.3 according to the invention with the lac promoter plasmid pASK84-D1.3 (Skerra (1994), supra) using *E. coli* K12-JM83 (Yanisch-Perron et al., Gene 33 (1985), 103–119) as a host strain showed that the yield obtained with the tetA promoter was the same as that obtained with the lacUV5 promoter. The time course of expression and the total amount of synthesized protein was also essentially the same in both systems. However, in the case of the lacUV5 plasmid small amounts of the Fab fragment could also be detected in the absence of the inducer IPTG.

Since secretion of an Ig fragment has a toxic effect in *E. coli,* the extent of repression in a promoter system can be determined in a qualitative manner on the basis of the viability and the growth behaviour of the transformed bacteria. For this purpose various host strains were transformed with pASK85-D1.3. In contrast to the lacUV5 promoter plasmid pASK84-D1.3 there was no indication of toxicity e.g. the occurrence of satellite colonies on ampicillin agar plates or lysis of overnight cultures when using numerous different *E. coli* strains. Moreover the cell densities of overnight cultures (at 37° C.) using the tetracycline promoter plasmid were reproducibly higher and the plasmid preparations always gave good yields. It was also possible to produce large amounts of single-stranded phagemid-DNA from the tet promoter vectors using standard methods which is a further indication for the efficient repression of the foreign gene.

Figure 4B:
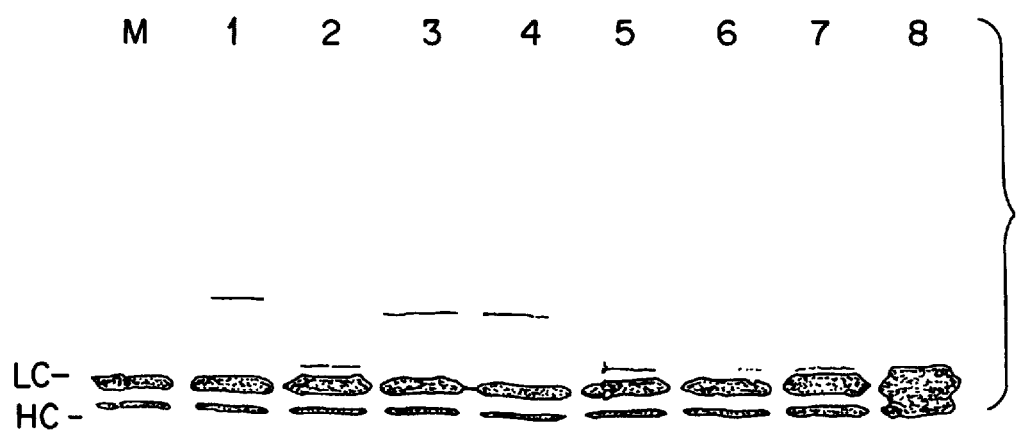

FIG. 4b shows the result of experiments on the expression of the recombinant Fab fragment in various *E. coli* host strains of the classes K12 or B.

A recombinant Fab fragment was detected in FIG. 4b by means of a Western blot of the total *E. coli* cell protein 3 hours after induction as in FIG. 4a. Lane 1: JM83 (Yanisch-Perron et al. (1985) supra), lane 2: WK6 (Zell and Fritz, EMBO J. 6 (1987), 1809–1815, lane 3: *E. coli* B (ATCC 11303), lane 4: BL21 (Studier and Moffat (1986), J. Mol. Biol. 189 (1986), 113–130), lane 5: MG1655 (Jensen, J. Bacteriol. 175 (1993), 3401–3407), lane 6: W3110 (Jensen (1993), supra), lane 7: W3110 in glucose minimal medium, lane 8: XL1-blue (Bullock et al., Biotechniques 5 (1987), 376–379), lane M: ca. 1 μg purified recombinant Fab fragment.

FIG. 4b shows that almost identical amounts of the recombinant Fab fragment were synthesized independently of the *E. coli* host strain. A complete induction of the promoter was found in this system with 100 or 200 μg/l anhydrotetracycline. Under these conditions both chains of the recombinant Fab fragment were processed quantitatively and also secreted into the periplasm. In addition it is also found that the expression of the recombinant Fab fragment is impaired neither by the presence of an episomal copy of the Tn10 tetracycline resistance gene (strain *E. coli* XL1-blue) nor when cultured in a glucose minimal medium.

Example 3

Gene Expression in a 4 l Fermenter

The use of minimal media with a defined composition is a particularly favourable prerequisite for the culture of the transformed bacterial cells up to a high cell density in the fermenter (Riesenberg, Curr. Opin. Biotechnol. 2 (1991), 380–384). For this purpose it is desirable to use a bacterial strain which does not have any auxotrophies. The property of the promoter system according to the invention of being able to function largely independently of the nutrient medium as well as of the characteristics of the *E. coli* strain is particularly advantageous in this connection.

The production of the artificial antibody Fab fragment M41 was examined in a 4 liter fermenter in the presence of a glucose minimal medium (Sambrook et al., supra) to which mineral salts and 100 mg per liter ampicillin to select for the expression plasmid were added. The expression plasmid pASK85-M41 used was constructed similarly to the plasmid pASK85-D1.3 but the variable domains of the coded antibody Fab fragment had another sequence. By plating samples on agar culture plates in the presence and absence of ampicillin it was proven that no loss of the expression plasmid occurs in the culture even at high cell density. When the gene expression was induced at a cell density OD(550)=10 by addition of 0.5 mg per liter anhydrotetracycline for 3 hours, the yields of the recombinant protein relative to the cell mass obtained were comparable to culturing in a shaking flask in the presence of complete medium.

We claim:

1. A prokaryotic vector comprising (a) a regulatable expression control sequence which can be repressed by a tetracycline repressor protein and (b) a DNA encoding a tetracycline repressor protein in operative linkage with an expression control sequence which cannot be repressed by a tetracycline repressor protein.

2. The vector according to claim 1, wherein said expression control sequence that can be repressed by a tetracycline repressor protein contains the nucleotide sequence shown in SEQ ID NO. 1.

3. The vector according to claim 1, wherein the expression control sequence that can be repressed by a tetracycline repressor protein contains the base sequences
5'-ACTCTATCATTGATAGAGT-3' [SEQ ID NO.3] and/or
5'-TCCCTATCAGTGATAGAGA-3' [SEQ ID NO.8].

4. The vector according to claim 1, wherein the tetracycline repressor coding sequence is in operative linkage with a constitutive expression control sequence.

5. The vector according to claim 1, wherein said vector is a circular plasmid.

6. The vector according to claim 1, further comprising a multiple cloning site which permits the insertion of at least one gene encoding a heterologous polypeptide, wherein said gene encoding said heterologous polypeptide is in operative linkage with the expression control sequence that can be repressed by a tetracycline repressor protein.

7. The vector according to claim 1, further comprising a signal peptide coding sequence in operative linkage with said gene encoding said heterologous polypeptide.

8. The vector according to claim 7, wherein the sequence coding for the signal peptide is an OmpA or PhoA signal sequence.

9. The vector according to claim 1, further comprising a transcription termination sequence in operative linkage with the expression control sequence that can be repressed by a tetracycline repressor protein.

10. The vector according to claim 9, wherein the transcription termination sequence is a lipoprotein transcription terminator.

11. The vector according to claim 1, further comprising a nucleotide sequence coding for an affinity peptide in operative linkage with the expression control sequence that can be repressed by a tetracycline repressor protein.

12. The vector according to claim 11, wherein the nucleotide sequence coding for the affinity peptide codes for an oligo-histidine peptide or for a streptavidin binding peptide.

13. The vector according to claim 1, further comprising at least one coding sequence coding for a heterologous polypeptide in operative linkage with the expression control sequence that can be repressed by a tetracycline repressor protein.

14. The vector according to claim 13, wherein the coding sequence codes for a polypeptide which is toxic to a prokaryotic cell.

15. The vector according to claim 13, wherein the coding sequence codes for an antibody fragment chain or the serum retinol binding protein.

16. The plasmid pASK75 having the nucleotide sequence shown in SEQ ID NO.2.

17. A prokaryotic cell containing (a) a gene coding for a heterologous polypeptide in operative linkage with a regulatable expression control sequence which can be repressed by a tetracycline repressor protein and (b) a DNA encoding a tetracycline repressor protein in operative linkage with an expression control sequence which cannot be repressed by a tetracycline repressor protein, wherein said cell is transformed with at least one copy of a vector comprising (a) a DNA encoding a regulatable expression control sequence which can be repressed by a tetracycline repressor protein and (b) a tetracycline repressor protein in operative linkage with an expression control sequence which cannot be repressed by a tetracycline repressor protein.

18. The cell according to claim 17, wherein said cell is an E. coli cell.

19. A process for the production of polypeptides in a prokaryotic cell by genetic engineering, comprising the steps of:

transforming a cell with (a) at least one gene coding for a heterologous polypeptide in operative linkage with a regulatable expression control sequence that can be repressed by a tetracycline repressor protein and (b) a DNA encoding a tetracycline repressor protein in operative linkage with an expression control sequence that cannot be repressed by a tetracycline repressor protein, culturing said cell under conditions which lead to an expression of the gene coding for the heterologous peptide, and isolating the heterologous polypeptide from the cell or from the medium.

20. The process according to claim 19, wherein said regulatable expression control sequence and said tetracycline repressor coding sequence are on a single vector.

21. The process according to claim 19, wherein the cell is cultured until a predetermined cell density is reached under conditions such that the expression of the gene coding for the heterologous polypeptide is repressed and then the expression of the gene is completely or partially induced by the addition of an inducer.

22. The process according to claim 21, wherein said inducer is selected from the group consisting of tetracycline and a tetracycline derivative.

23. The process according to claim 22, wherein said inducer is anhydrotetracycline.

24. The process according to claim 21, wherein said inducer is added to the medium up to a final concentration of 5 to 500 µg/l medium.

25. The process according to claim 21, wherein the cell is cultured in a minimal medium.

* * * * *

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 83 base pairs
        ( B ) TYPE: nucleic acid
        ( C ) STRANDEDNESS: both
        ( D ) TOPOLOGY: linear ( x i ) SEQUENCE DESCRIPTION: SEQ ID NO: 1:

```
ATTAATTCCT  AATTTTTGTT  GACACTCTAT  CATTGATAGA  GTTATTTTAC  CACTCCCTAT      60

CAGTGATAGA  GAAAAGTGAA  ATG                                                 83
```

( 2 ) INFORMATION FOR SEQ ID NO: 2:

( i ) SEQUENCE CHARACTERISTICS:
    ( A ) LENGTH: 3266 base pairs
    ( B ) TYPE: nucleic acid
    ( C ) STRANDEDNESS: double
    ( D ) TOPOLOGY: circular ( x i ) SEQUENCE DESCRIPTION: SEQ ID NO: 2:

| | | | | | | |
|---|---|---|---|---|---|---|
| ACCCGACACC | ATCGAATGGC | CAGATGATTA | ATTCCTAATT | TTTGTTGACA | CTCTATCATT | 60 |
| GATAGAGTTA | TTTTACCACT | CCCTATCAGT | GATAGAGAAA | AGTGAAATGA | ATAGTTCGAC | 120 |
| AAAAATCTAG | ATAACGAGGG | CAAAAAATGA | AAAAGACAGC | TATCGCGATT | GCAGTGGCAC | 180 |
| TGGCTGGTTT | CGCTACCGTA | GCGCAGGCCT | GAGACCAGAA | TTCGAGCTCG | GTACCCGGGG | 240 |
| ATCCCTCGAG | GTCGACCTGC | AGGCAGCGCT | TGGCGTCACC | CGCAGTTCGG | TGGTTAATAA | 300 |
| GCTTGACCTG | TGAAGTGAAA | AATGGCGCAC | ATTGTGCGAC | ATTTTTTTG | TCTGCCGTTT | 360 |
| ACCGCTACTG | CGTCACGGAT | CTCCACGCGC | CCTGTAGCGG | CGCATTAAGC | GCGGCGGGTG | 420 |
| TGGTGGTTAC | GCGCAGCGTG | ACCGCTACAC | TTGCCAGCGC | CCTAGCGCCC | GCTCCTTTCG | 480 |
| CTTTCTTCCC | TTCCTTTCTC | GCCACGTTCG | CCGGCTTTCC | CCGTCAAGCT | CTAAATCGGG | 540 |
| GGCTCCCTTT | AGGGTTCCGA | TTTAGTGCTT | TACGGCACCT | CGACCCCAAA | AAACTTGATT | 600 |
| AGGGTGATGG | TTCACGTAGT | GGGCCATCGC | CCTGATAGAC | GGTTTTCGC | CCTTTGACGT | 660 |
| TGGAGTCCAC | GTTCTTTAAT | AGTGGACTCT | TGTTCCAAAC | TGGAACAACA | CTCAACCCTA | 720 |
| TCTCGGTCTA | TTCTTTTGAT | TTATAAGGGA | TTTTGCCGAT | TTCGGCCTAT | TGGTTAAAAA | 780 |
| ATGAGCTGAT | TTAACAAAAA | TTTAACGCGA | ATTTTAACAA | AATATTAACG | TTTACAATTT | 840 |
| CAGGTGGCAC | TTTTCGGGGA | AATGTGCGCG | GAACCCCTAT | TTGTTTATTT | TTCTAAATAC | 900 |
| ATTCAAATAT | GTATCCGCTC | ATGAGACAAT | AACCCTGATA | AATGCTTCAA | TAATATTGAA | 960 |
| AAAGGAAGAG | TATGAGTATT | CAACATTTCC | GTGTCGCCCT | TATTCCCTTT | TTTGCGGCAT | 1020 |
| TTTGCCTTCC | TGTTTTTGCT | CACCCAGAAA | CGCTGGTGAA | AGTAAAAGAT | GCTGAAGATC | 1080 |
| AGTTGGGTGC | ACGAGTGGGT | TACATCGAAC | TGGATCTCAA | CAGCGGTAAG | ATCCTTGAGA | 1140 |
| GTTTTCGCCC | CGAAGAACGT | TTTCCAATGA | TGAGCACTTT | TAAAGTTCTG | CTATGTGGCG | 1200 |
| CGGTATTATC | CCGTATTGAC | GCCGGGCAAG | AGCAACTCGG | TCGCCGCATA | CACTATTCTC | 1260 |
| AGAATGACTT | GGTTGAGTAC | TCACCAGTCA | CAGAAAAGCA | TCTTACGGAT | GGCATGACAG | 1320 |
| TAAGAGAATT | ATGCAGTGCT | GCCATAACCA | TGAGTGATAA | CACTGCGGCC | AACTTACTTC | 1380 |
| TGACAACGAT | CGGAGGACCG | AAGGAGCTAA | CCGCTTTTTT | GCACAACATG | GGGGATCATG | 1440 |
| TAACTCGCCT | TGATCGTTGG | GAACCGGAGC | TGAATGAAGC | CATACCAAAC | GACGAGCGTG | 1500 |
| ACACCACGAT | GCCTGTAGCA | ATGGCAACAA | CGTTGCGCAA | ACTATTAACT | GGCGAACTAC | 1560 |
| TTACTCTAGC | TTCCCGGCAA | CAATTGATAG | ACTGGATGGA | GGCGGATAAA | GTTGCAGGAC | 1620 |
| CACTTCTGCG | CTCGGCCCTT | CCGGCTGGCT | GGTTTATTGC | TGATAAATCT | GGAGCCGGTG | 1680 |
| AGCGTGGCTC | TCGCGGTATC | ATTGCAGCAC | TGGGGCCAGA | TGGTAAGCCC | TCCCGTATCG | 1740 |
| TAGTTATCTA | CACGACGGGG | AGTCAGGCAA | CTATGGATGA | ACGAAATAGA | CAGATCGCTG | 1800 |
| AGATAGGTGC | CTCACTGATT | AAGCATTGGT | AGGAATTAAT | GATGTCTCGT | TTAGATAAAA | 1860 |
| GTAAAGTGAT | TAACAGCGCA | TTAGAGCTGC | TTAATGAGGT | CGGAATCGAA | GGTTTAACAA | 1920 |
| CCCGTAAACT | CGCCCAGAAG | CTAGGTGTAG | AGCAGCCTAC | ATTGTATTGG | CATGTAAAAA | 1980 |
| ATAAGCGGGC | TTTGCTCGAC | GCCTTAGCCA | TTGAGATGTT | AGATAGGCAC | CATACTCACT | 2040 |
| TTTGCCCTTT | AGAAGGGGAA | AGCTGGCAAG | ATTTTTTACG | TAATAACGCT | AAAAGTTTTA | 2100 |

```
GATGTGCTTT  ACTAAGTCAT  CGCGATGGAG  CAAAAGTACA  TTTAGGTACA  CGGCCTACAG    2160

AAAAACAGTA  TGAAACTCTC  GAAAATCAAT  TAGCCTTTTT  ATGCCAACAA  GGTTTTTCAC    2220

TAGAGAATGC  ATTATATGCA  CTCAGCGCAG  TGGGGCATTT  TACTTTAGGT  TGCGTATTGG    2280

AAGATCAAGA  GCATCAAGTC  GCTAAAGAAG  AAAGGGAAAC  ACCTACTACT  GATAGTATGC    2340

CGCCATTATT  ACGACAAGCT  ATCGAATTAT  TTGATCACCA  AGGTGCAGAG  CCAGCCTTCT    2400

TATTCGGCCT  TGAATTGATC  ATATGCGGAT  TAGAAAAACA  ACTTAAATGT  GAAAGTGGGT    2460

CTTAAAAGCA  GCATAACCTT  TTTCCGTGAT  GGTAACTTCA  CTAGTTTAAA  AGGATCTAGG    2520

TGAAGATCCT  TTTTGATAAT  CTCATGACCA  AAATCCCTTA  ACGTGAGTTT  TCGTTCCACT    2580

GAGCGTCAGA  CCCCGTAGAA  AAGATCAAAG  GATCTTCTTG  AGATCCTTTT  TTTCTGCGCG    2640

TAATCTGCTG  CTTGCAAACA  AAAAAACCAC  CGCTACCAGC  GGTGGTTTGT  TTGCCGGATC    2700

AAGAGCTACC  AACTCTTTTT  CCGAAGGTAA  CTGGCTTCAG  CAGAGCGCAG  ATACCAAATA    2760

CTGTCCTTCT  AGTGTAGCCG  TAGTTAGGCC  ACCACTTCAA  GAACTCTGTA  GCACCGCCTA    2820

CATACCTCGC  TCTGCTAATC  CTGTTACCAG  TGGCTGCTGC  CAGTGGCGAT  AAGTCGTGTC    2880

TTACCGGGTT  GGACTCAAGA  CGATAGTTAC  CGGATAAGGC  GCAGCGGTCG  GGCTGAACGG    2940

GGGGTTCGTG  CACACAGCCC  AGCTTGGAGC  GAACGACCTA  CACCGAACTG  AGATACCTAC    3000

AGCGTGAGCT  ATGAGAAAGC  GCCACGCTTC  CCGAAGGGAG  AAAGGCGGAC  AGGTATCCGG    3060

TAAGCGGCAG  GGTCGGAACA  GGAGAGCGCA  CGAGGGAGCT  TCCAGGGGGA  AACGCCTGGT    3120

ATCTTTATAG  TCCTGTCGGG  TTTCGCCACC  TCTGACTTGA  GCGTCGATTT  TTGTGATGCT    3180

CGTCAGGGGG  GCGGAGCCTA  TGGAAAAACG  CCAGCAACGC  GGCCTTTTTA  CGGTTCCTGG    3240

CCTTTTGCTG  GCCTTTTGCT  CACATG                                           3266
```

( 2 ) INFORMATION FOR SEQ ID NO: 3:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 3:

```
ACTCTATCAT  TGATAGAGT                                                      19
```

( 2 ) INFORMATION FOR SEQ ID NO: 4:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( x i ) SEQUENCE DESCRIPTION: SEQ ID NO: 4:

```
TCCCTATCAG  TGATAG                                                         16
```

( 2 ) INFORMATION FOR SEQ ID NO: 5:

( i ) SEQUENCE CHARACTERISTICS:
        ( A ) LENGTH: 10 amino acids
        ( B ) TYPE: amino acid
        ( D ) TOPOLOGY: linear ( x i ) SEQUENCE DESCRIPTION: SEQ ID NO: 5:

```
Ser  Ala  Trp  Arg  His  Pro  Gln  Phe  Gly  Gly
                  5                        10
```

(2) INFORMATION FOR SEQ ID NO: 6:

(i) SEQUENCE CHARACTERISTICS:
(A) LENGTH: 375 base pairs
(B) TYPE: nucleic acid
(C) STRANDEDNESS: double
(D) TOPOLOGY: linear (xi) SEQUENCE DESCRIPTION: SEQ ID NO: 6:

| | | | | | | |
|---|---|---|---|---|---|---|
| CCATCGAATG | GCCAGATGAT | TAATTCCTAA | TTTTGTTGA | CACTCTATCA | TTGATAGAGT | 60 |
| TATTTTACCA | CTCCCTATCA | GTGATAGAGA | AAAGTGAAAT | GAATAGTTCG | ACAAAAATCT | 120 |
| AGATAACGAG | GGCAAAAAAT | GAAAAAGACA | GCTATCGCGA | TTGCAGTGGC | ACTGGCTGGT | 180 |
| TTCGCTACCG | TAGCGCAGGC | CTGAGACCAG | AATTCGAGCT | CGGTACCCGG | GGATCCCTCG | 240 |
| AGGTCGACCT | GCAGGCAGCG | CTTGGCGTCA | CCCGCAGTTC | GGTGGTTAAT | AAGCTTGACC | 300 |
| TGTGAAGTGA | AAAATGGCGC | ACATTGTGCG | ACATTTTTT | TGTCTGCCGT | TTACCGCTAC | 360 |
| TGCGTCACGG | ATCTC | | | | | 375 |

(2) INFORMATION FOR SEQ ID NO: 7:

(i) SEQUENCE CHARACTERISTICS:
(A) LENGTH: 75 base pairs
(B) TYPE: nucleic acid
(C) STRANDEDNESS: double
(D) TOPOLOGY: linear (xi) SEQUENCE DESCRIPTION: SEQ ID NO: 7:

| | | | | | | |
|---|---|---|---|---|---|---|
| AGATAGGTGC | CTCACTGATT | AAGCATTGGT | AGGAATTAAT | GATGTCTCGT | TTAGATAAAA | 60 |
| GTAAAGTGAT | TAACA | | | | | 75 |

(2) INFORMATION FOR SEQ ID NO: 8:

(i) SEQUENCE CHARACTERISTICS:
(A) LENGTH: 19 base pairs
(B) TYPE: nucleic acid
(C) STRANDEDNESS: double
(D) TOPOLOGY: linear (xi) SEQUENCE DESCRIPTION: SEQ ID NO: 8:

TCCCTATCAG TGATAGAGA    19